United States Patent
Alberg et al.

(10) Patent No.: US 6,526,631 B1
(45) Date of Patent: Mar. 4, 2003

(54) PERFORATED RELEASE TAPE

(75) Inventors: Randall Lynn Alberg, Maplewood, MN (US); Gerhard Ludwig Richter, Erkelenz (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/566,435

(22) Filed: May 8, 2000

Related U.S. Application Data

(63) Continuation-in-part of application No. 09/499,136, filed on Feb. 7, 2000, now Pat. No. 6,363,587.

(51) Int. Cl.$^7$ .................................................. A61F 13/56
(52) U.S. Cl. ........................................ 24/306; 604/391
(58) Field of Search ...................... 24/306, 304, 442, 24/DIG. 4; 604/391; 428/100

(56) References Cited

U.S. PATENT DOCUMENTS

| | | | |
|---|---|---|---|
| 3,800,796 A | * 4/1974 | Jacob | 604/369 |
| 3,848,594 A | 11/1974 | Buell | 128/284 |
| 4,074,716 A | * 2/1978 | Schaar | 24/304 |
| 4,643,729 A | * 2/1987 | Laplanche | 604/389 |
| 4,726,971 A | 2/1988 | Pape et al. | 428/40 |
| 5,176,670 A | 1/1993 | Roessler et al. | 604/391 |
| 5,256,231 A | 10/1993 | Gorman et al. | 156/178 |
| 5,779,691 A | * 7/1998 | Schmitt | 156/183 |
| 5,926,926 A | 7/1999 | Kato | 24/442 |
| 6,363,587 B1 | * 4/2002 | Richter et al. | 24/306 |

FOREIGN PATENT DOCUMENTS

| | | |
|---|---|---|
| EP | 0 321 232 B1 | 5/1993 |
| EP | 0 818 188 A2 | 1/1998 |
| EP | 0 832 631 A2 | 1/1998 |
| EP | 0 853 935 A2 | 7/1998 |
| EP | 0 894 448 A1 | 2/1999 |
| EP | 0 927 550 | 7/1999 |
| EP | 0 941 730 | 9/1999 |
| FR | 2807939 A1 | 10/2000 |
| JP | 8-2365 | 1/1996 |
| JP | 8-187113 | * 7/1996 |
| JP | 10-137008 | 5/1998 |
| WO | WO 96/12464 | 5/1996 |
| WO | WO 97/28774 | 8/1997 |
| WO | WO 99/48455 | * 9/1999 |

* cited by examiner

*Primary Examiner*—James R. Brittain
(74) *Attorney, Agent, or Firm*—Gary L. Griswold; Robert W. Sprague; William J. Bond

(57) ABSTRACT

There is provided a mechanical fastener tape tab laminate capable of remaining closed until needed for use on a disposable garment. A tape tab backing had at least a first distal end portion, an inner tab portion and second distal end portion. The second distal end portion is provided with a mechanical fastener material. The first distal end portion is provided with an adhesive layer for permanent attachment to the disposable absorbent article. The tape tab backing laminate further has a folded tape portion comprising a backing having an adhesive layer on an outer face and at least an inner leg portion and an outer leg portion. The outer leg portion has an exposed adhesive provided for permanent attachment to the disposable absorbent article. The inner leg portion is attached to the tape tab backing so that the folded tape portion keeps the second distal end folded onto the first distal end. The inner and outer leg portions are separated by at least one fold. The folded tape portion backing is provided with a line of weakness along the at least one fold, wherein the line of weakness is provided on a portion of the tape tab backing spaced from the first distal end portion. When the laminate is ready for use, the folded tape portion is broken at the line of weakness allowing the second distal end to be unfolded from the first distal end.

10 Claims, 8 Drawing Sheets

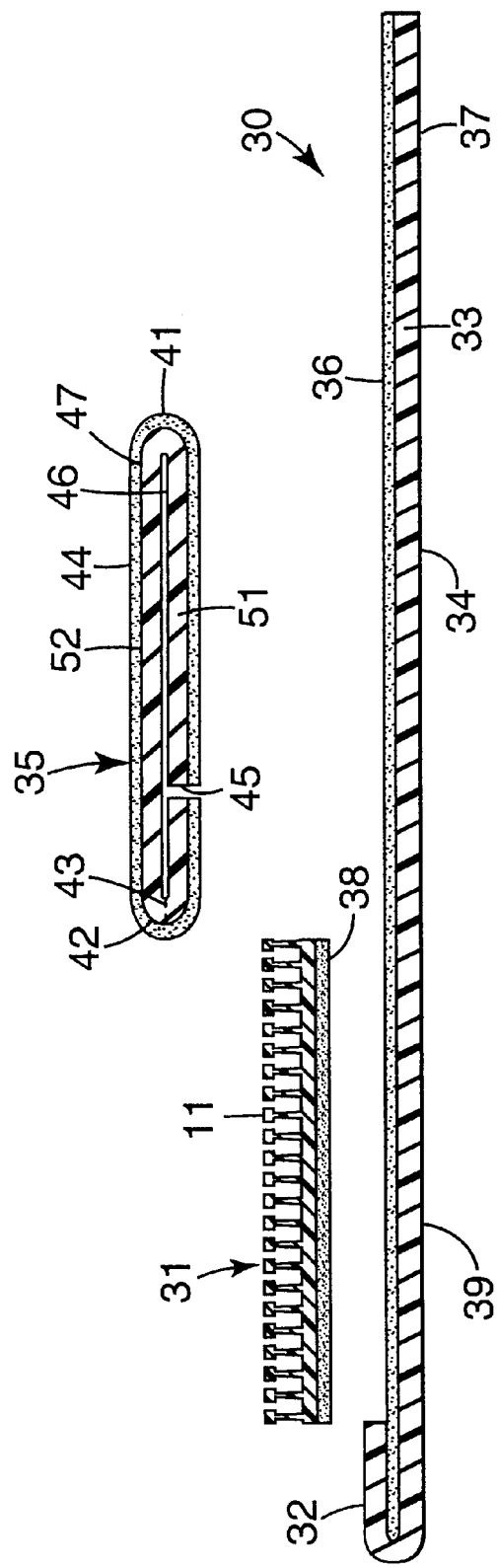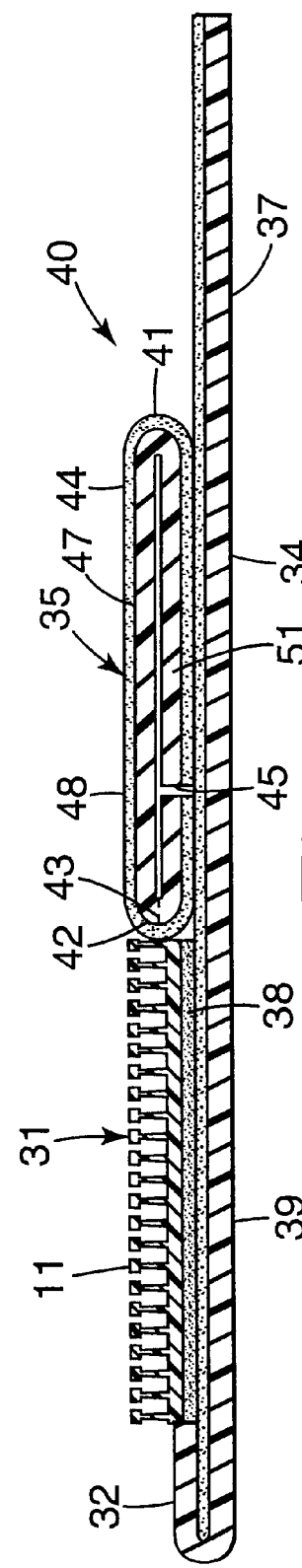

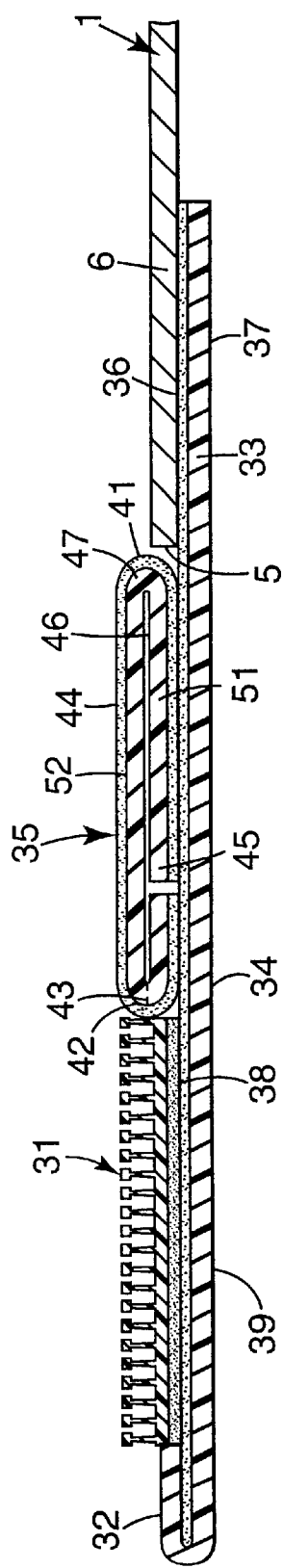
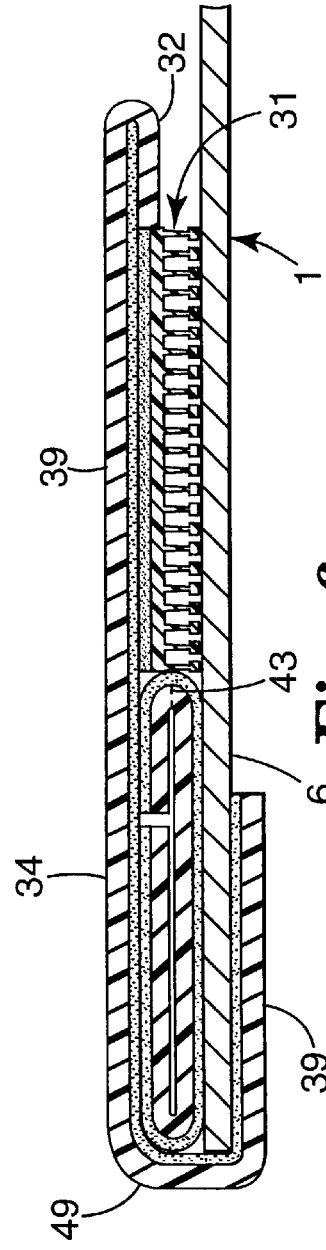
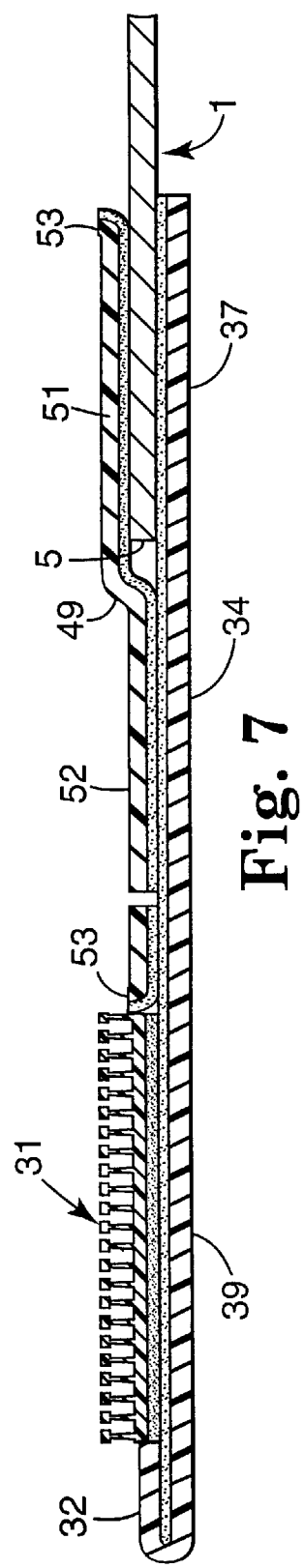

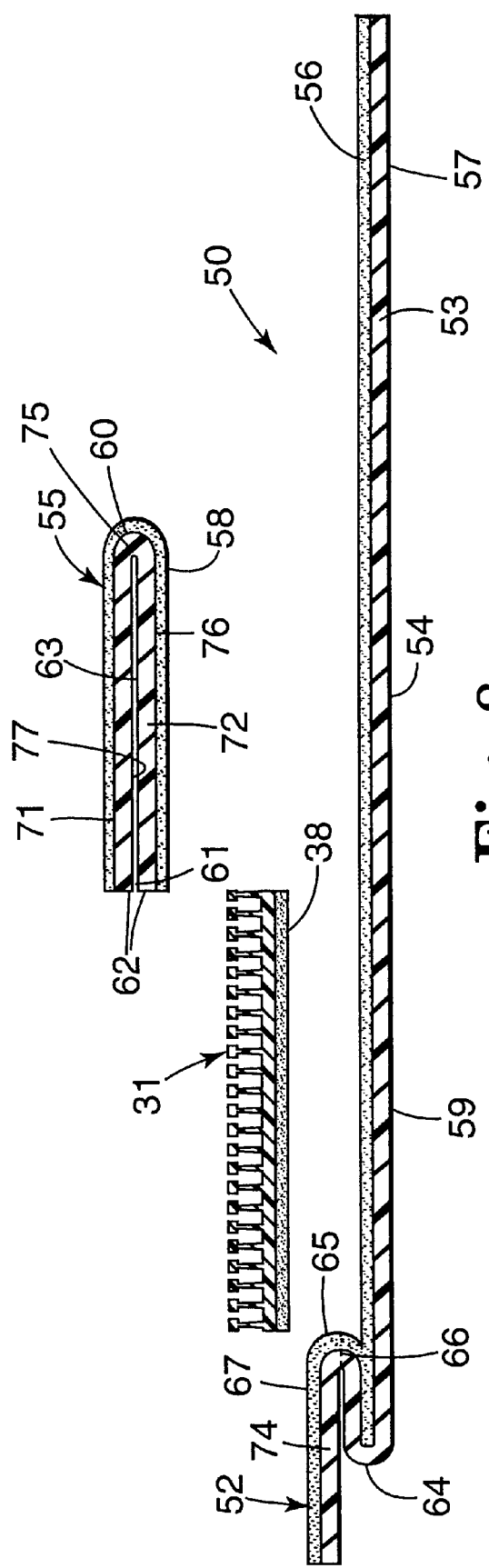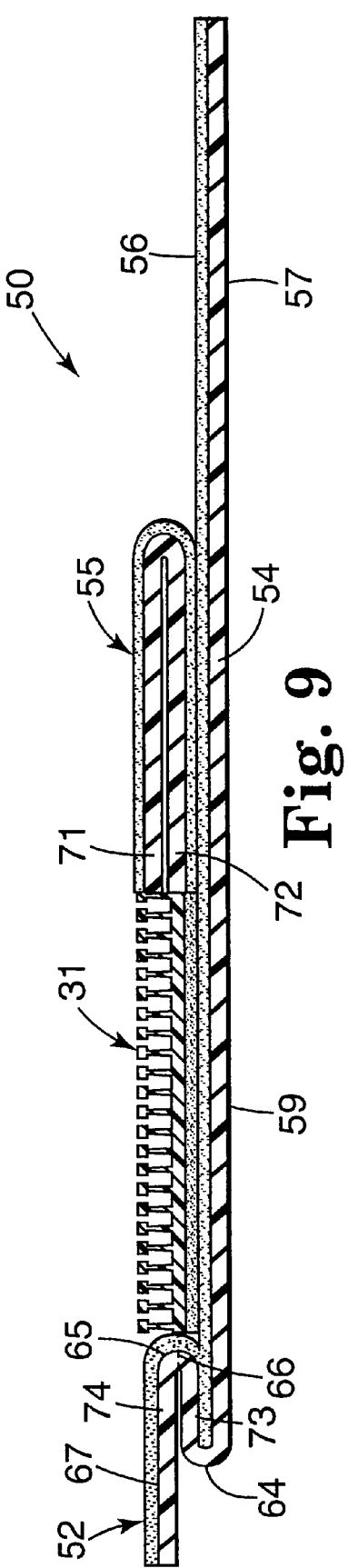

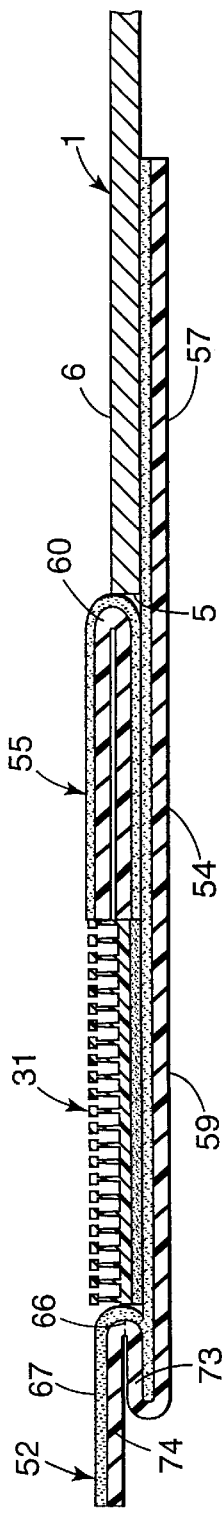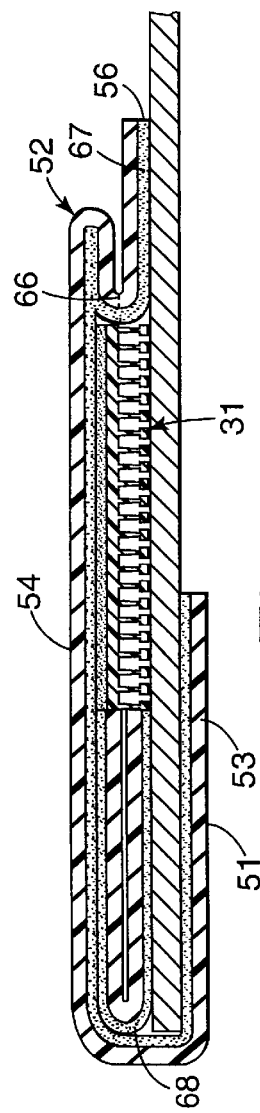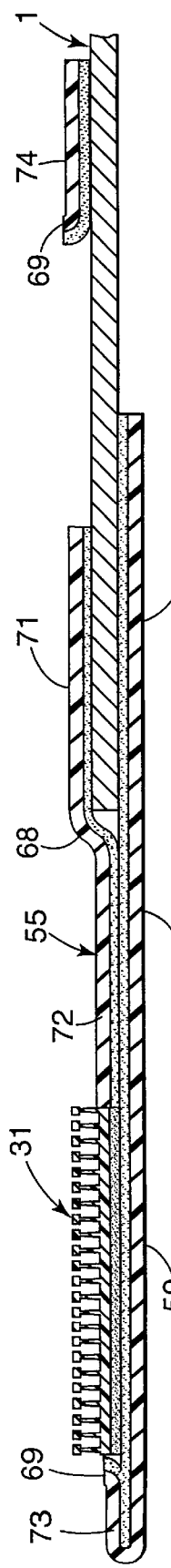

PERFORATED RELEASE TAPE

CROSS-REFERENCE TO RELATED APPLICATIONS

This is a continuation-in-part of application Ser. No. 09/499,136, filed Feb. 7, 2000 now U.S. Pat. No 6,363,587.

BACKGROUND AND FIELD OF INVENTION

The present invention relates to a mechanical fastener closure tape tab laminate for use on disposable articles, generally a disposable absorbent diaper.

Closure tape tab laminates utilizing mechanical fasteners are known in the art with the mechanical fastener generally located on a tape tab backing. The mechanical fastener is attached generally by the use of adhesives. The opposite end of the tab is generally permanently attached to one face of the disposable article with the mechanical fastener extending out beyond a side edge of the absorbent article for use in forming a closure with a mating attachment provided on a opposite end of the disposable article. Generally when the diaper or the like is packaged prior to use, it is preferred that the tab be folded back into the main body of the diaper. Otherwise the tab will extend out beyond the edge of the diaper and create problems such as inadvertently attaching to substrates as well as making it difficult to fold the article into a form suitable for an easily packaged product. As such, it is preferred that the mechanical fastener "free end" be folded back onto the opposite face of the diaper prior to use. The problem of an unattached tab extending out beyond the edge of the diaper is generally known as flagging. The conventional approach to solving this flagging problem has been to provide a pressure sensitive adhesive somewhere on the tape tab laminate which would allow the tape tab free end to releasably adhere to a suitable surface on the diaper. The end user would then grasp a fingerlift on the tab and break this adhesive bond and extend the tab for use. Such an adhesive antiflagging configuration is disclosed, for example, in European Patent No. 321,232, where the adhesive is adjacent the mechanical fastener on the tab. European Patent Application No. 894,448 discloses providing pressure sensitive adhesive on the tops of mechanical fastener hook heads for antiflagging. Japanese Patent Application No. 8-2365 provides adhesive on the extended portion of the tab, which adhesive then transfers to the diaper such that there is no exposed adhesive on the free end of the tab when in use. The use of an exposed adhesive for antiflagging is also taught in PCT Patent Application No. WO97/28774. Although effective, the use of an exposed pressure sensitive adhesive is undesirable in many instances with a mechanical fastening system. For example there are many exposed fibrous surfaces on absorbent articles with mechanical fasteners, which fibrous surfaces can cause fiber contamination of the adhesive. Also there is undesirable reaction on the part of some customers to the use of exposed adhesives in mechanical fastener systems of this type. For these reasons and others there has been considerable work on a non-adhesive solution to the flagging problem.

The use of a non-adhesive approach to the flagging problem is proposed, for example, in European Patent Application No. 818,188. This patent document proposes releasably welding the tab free end to an inner surface of a diaper. Although effective, this is problematic in that it requires an on-line welding during the diaper manufacturing process, which can slow diaper production. Japanese Patent Application No. 10-137008 and U.S. Pat. No. 5,926,926 disclose the use of a separate small patch of loop material, which can engage with the hooks. These loop patches are generally placed where the antiflagging adhesive would be placed. The small loop patches suggested in these patents are unlikely to be entirely effective in providing for a reliable connection. Also these loops add significant bulk to the tabs creating the possibility of hard bands in the packaged diapers and making it difficult to provide long yardage rolls of prelaminated mechanical fastener tape tabs. European Patent Application No. 832,631 proposes a complicated structure involving a splitable nonwoven material. This would have similar issues as the use of loop patches and be difficult to manufacture. European Patent Application No. 853,935 discloses a complicated laminated tab structure, which comprises a tape tab backing having two adhesive coated portions with an adhesive free region separating them and a separate carrier for the hook. The hook carrier has a separate adhesive attachment zone and is perforated in an adhesive free zone. The carrier perforation is separable which allows the tab to be maintained in a folded condition prior to use and broken or torn to allow the tab to be extended. Although effective in maintaining a tab in a folded condition, this construction does not allow for a conventional Y-bond to provide a secure attachment to both faces of the diaper side edge and requires two complicated zone adhesive coatings on the tape tab backing and the carrier.

Although there are many varied techniques taught in the art to maintain a fastening tab laminate in a folding condition around the edge of a diaper prior to use, there still remains the need for an effective way of providing such an arrangement for a mechanical fastener tape tab laminate which provides for a combination of ease of construction, a reliable and secure attachment that is easily releasable by the user and which does not rely on exposed pressure sensitive adhesives and preferably in a construction that allows the possibility of providing a secure Y-bond to the edge of the diaper.

BRIEF DESCRIPTION OF THE DRAWINGS

FIG. 3 is an exploded view of the first embodiment of a mechanical fastener tape tab laminate of the invention.

FIG. 4 is an assembled view of the first embodiment mechanical fastener tape tab laminate.

FIG. 5 is an assembled view of the first embodiment mechanical fastener tape tab laminate when initially attached to an article.

FIG. 6 is an assembled view of the first embodiment mechanical fastener tape tab laminate when fully attached to an article.

FIG. 7 is an assembled view of the first embodiment mechanical fastener tape tab laminate in a use form.

FIG. 8 is an exploded view of a second embodiment of a mechanical fastener tape tab laminate of the invention.

FIG. 9 is an assembled view of the second embodiment of a mechanical fastener tape tab laminate of the invention.

FIG. 10 is an assembled view of the second embodiment of a mechanical fastener tape tab laminate of the invention when initially attached to an article.

FIG. 11 is an assembled view of the second embodiment of a mechanical fastener tape tab laminate of the invention when fully attached to an article.

FIG. 12 is an assembled view of the second embodiment of a mechanical fastener tape tab laminate of the invention in a use form.

DETAILED DESCRIPTION OF THE PREFERRED EMBODIMENTS

Figure 1:
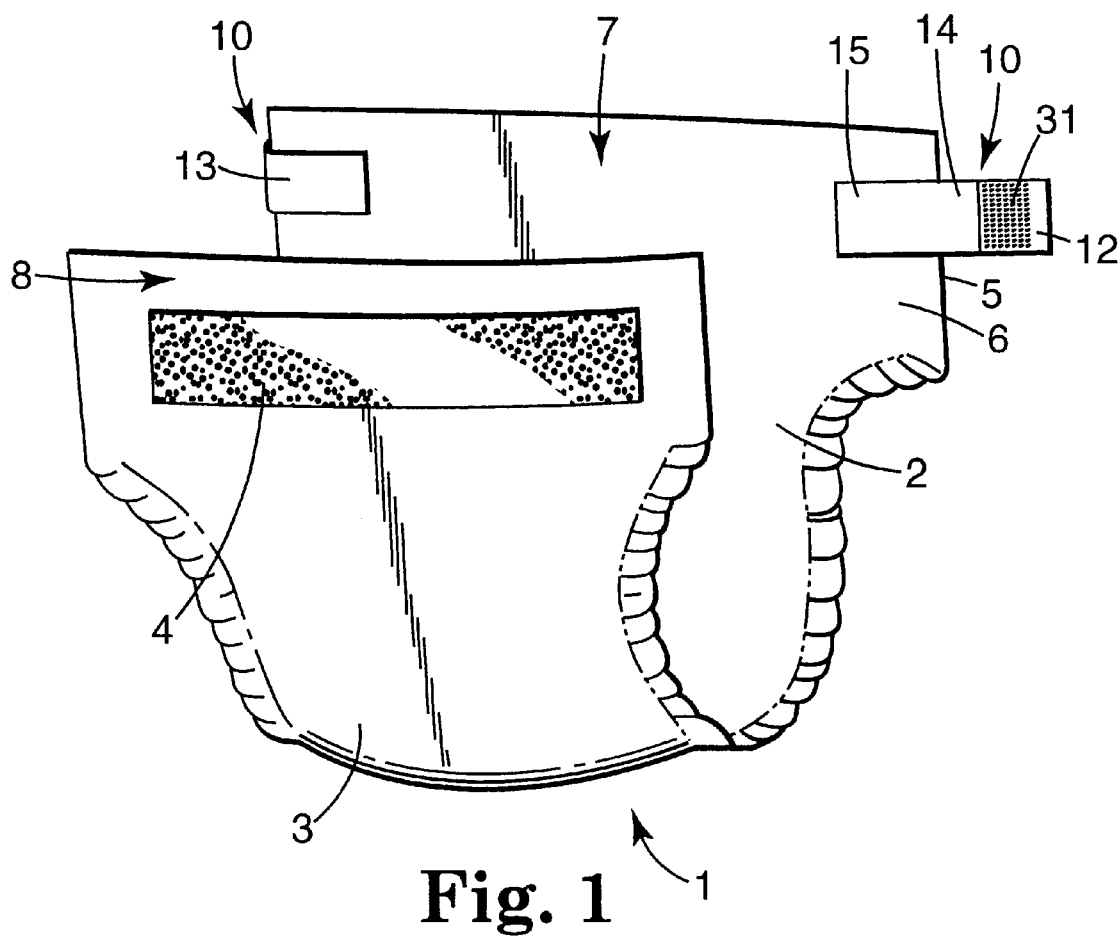
FIG. 1 is a perspective view of a diaper using a tape tab in accordance with the invention.

Referring to FIG. 1, a conventional diaper construction 1 is shown comprising a liquid permeable topsheet 2 and a liquid impermeable backsheet 3. Between the topsheet 2 and the backsheet 3 would be an absorbent pad structure (not shown). The liquid permeable topsheet 2 would generally be a nonwoven web or like permeable structure which would allow the passage of liquids to the absorbent pad. The liquid impermeable backsheet 3 conventionally is a film or a laminate of a film with a nonwoven. The backsheet film is generally a polyolefin thermoplastic film, which can be provided with breathability. The nonwoven laminated to such a film would be on the outer surface of the diaper to provide a soft texture and cloth-like feel. The nonwoven can also provide a surface that could allow a hook material to engage, in certain circumstances, to allow for closure attachment and/or disposability of the diaper following use. At least a first corner 6 at a first end 7 of the diaper chassis 1 has a mechanical fastener tab 10 designed to adhere to a mating mechanical fastener element 4, and/or the fibrous backsheet 3, at a second end 8 of the diaper chassis 1. When the diaper is worn, i.e., when the invention mechanical fastener closure tab is in use, the first corner 6 at the first end 7 of the disposable diaper overlap with a corresponding opposing corner 6 at the opposing end 8 of the diaper so that the corner positions of first end 7 and second end 8 of the diaper overlap. Generally mechanical fastening hooks engage with a loop structure and/or possibly the backsheet so that there is a continuous engagement with the waist of the wearer, encircling the torso.

The liquid permeable topsheet would comprise a conventional material known for this use. These materials include spunbond webs, melt blown webs, carded webs, and the like. These webs are conventionally formed of thermoplastic and hydrophobic polymer fibers, such as polyolefin or polyester fibers.

The backsheet 3 is a generally liquid impermeable web, optionally an air permeable web or film and conventionally uses a thin polyolefin polymer film generally less than 1 to 2 mils thick. For use in a mechanical fastener closure system, the backsheet 3 is preferably a laminate of a substantially liquid impermeable film with a woven, nonwoven, knitted or stitch bonded or like fibrous web, which fibrous web is suitably engageable with the mechanical fastener hooks 11 on the mechanical fastening tab 10. Adhesive lamination, pattern heat bonding or extrusion lamination of the web with the liquid impermeable film can form this laminate.

The loop material can be any conventional loop fabric such as disclosed, for example, in U.S. Pat. Nos. 5,176,670 or 5,256,231, the substance of which are incorporated herein by reference. The loop fabric can be a conventional fibrous structure such as a nonwoven, a knitted material, a stitch bonded material or the like, formed of natural or synthetic fibers, which fibers can be either continuous or discontinuous and/or bonded. Generally, the loop material must have sufficient available fibers and loft to allow penetration of the mechanical fastening 11 into the loop structure but still have enough fibers available to engage with the individual hooks.

Figure 2:
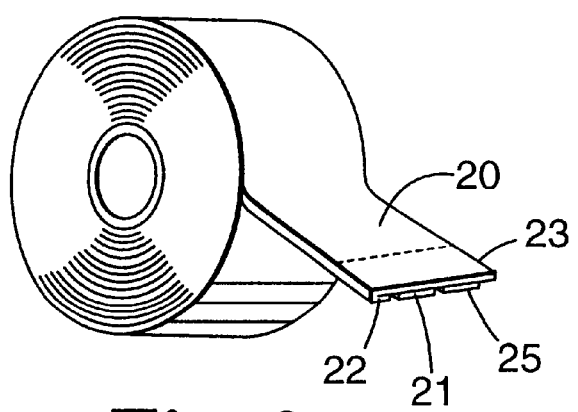
FIG. 2 is a perspective view of a diaper roll of a prelaminated mechanical fastener tape tab of the invention.

The mechanical fastener of the invention would generally comprise a tape backing 13 having a hook element 11 where the backing is provided with a distal finger-lift region 12. The backing 13 would further include a release tab 15 that would preferably cover an inner tab portion 14 of the tape tab backing and is preferably also bonded to the topsheet 2 at the corner portion 6 at the first end 7 of the diaper. Mechanical fastener tape tab laminates 10 of the invention can be provided in a roll form as is generally shown in FIG. 2. This roll is generally provided with a mechanical fastener tape tab laminate having a finger lift 22, a mechanical fastener portion 21 and a release tab 25. Individual tab elements 23 can be cut from the roll and attached to the diaper in a manner which will become clear upon discussion of the further specific embodiments below.

A first embodiment of the invention mechanical fastener tape tab laminate is shown in the expanded view of FIG. 3. The tape tab backing 33 is provided with a pressure-sensitive adhesive layer 36, which adhesive layer allows for attachment of the mechanical fastener material 31 and the release tab 35. Optionally, a further adhesive layer 38 can be provided on the mechanical fastener material 31. The tape tab backing 33 is separated into three distinct portions. The first distal end portion 37 is provided with an exposed portion of the adhesive layer 36, which exposed adhesive is used for permanent attachment of the assembled tab to one face of the diaper chassis 1. An inner tab portion 34 is attached to the release tab 35 using the adhesive layer, 36 and 44. A second distal end portion 39 of the tape tab backing 33 is provided with the releasably fastenable mechanical fastener material 31 and optionally a finger lift 32. The mechanical fastener material 31 is attached using adhesive layer 36 and/or an adhesive layer 38 on the mechanical fastener element 31. Generally, the tape tab backing 33 is provided with a continuous pressure-sensitive adhesive layer 36 for ease of manufacturability. However, the inner tab portion 34 and the second distal end portion 39 need not be provided with pressure-sensitive adhesive provided that the mechanical fastener material 31 and/or the release tab 35 are provided with suitable adhesives or other conventional attachment means to attach to the backing 33. Generally, pressure-sensitive adhesives are preferred for attachment of the mechanical fastener material 31 and release tab 35, however, other suitable conventional methods, such as thermal point bonding or heat activatable adhesives could be used if suitable. In the preferred embodiment, the mechanical fastener material 31 is a hook element 11 generally provided with upstanding hook elements for engagement with a mating loop surface provided on the outside of the diaper, generally, the loop fastener element 4. Although generally not economically viable, alternatively, a loop fastening material could be used in place of the hook element 11 as the mechanical fastener material 31, provided a suitable hook material was provided on the front portion of the diaper 1. Other known mechanical fastening structures could also be suitable for the invention laminates such as self-mating fasteners.

The release tab 35 generally comprises a backing 47 provided with a pressure-sensitive adhesive layer 44 on the outer face. The opposite inner face 46 of the backing can be provided with a suitable release layer or treatment, however such a release layer or treatment is optional. The release tab 35 in the FIG. 3 embodiment is folded into a circular form provided with an inner fold 41 and an outer fold 42. The inner fold 41 would be adjacent the edge on a diaper 1 when the tab portion first distal end 37 is attached to the diaper (e.g., backsheet 3). Generally, the release tab 35 comprises a flat film, or like web, folded into a circular form having ends 45. These ends 45 meet to form the circular form on the side of the folded structure directly attached to the tape tab backing 33. Thus, both ends 45 are attached to the tape tab backing 33. This ensures that the release tab backing is a substantially continuous uninterrupted circular structure when the release tab is attached to the backing 33 in the laminate. Specifically, the release tab 35 is a substantially continuous (no gaps that would allow the release tab 35 to be opened or unfolded) structure, from the inner fold 41 to the outer fold 42 and back again, when the release tab 35 is attached to the tape tab backing 33 as shown in FIG. 4. The circular structure of the release tab when attached to the backing 33 has an outer leg 52 and an inner attached leg 51. The outer fold 42 is provided with a weakened zone 43 which allows the release tab to be easily broken at this point. Generally, this line of weakness is provided by suitably cutting the release tab backing 47 intermittently along the line 43 along the width dimension of the release tab backing. The backing 47 remains continuous and attached along this line of weakness to allow the release tab to be folded and remain folded and continuous prior to use. The line of weakness could also be formed by scoring, partially cutting through backing 47, or otherwise weakening backing 47 along line 43 across substantially the entire width of the backing 47.

FIG. 4 shows the assembled laminate as shown in the expanded view of FIG. 3, where like numerals indicate identical elements. The second distal end portion 39 of the tape tab backing 33 has been folded over onto itself to provide a finger lift portion 32 and the mechanical fastener material 31 and the release tab 35 are in substantially abutting relationship. This allows the mechanical fastener material 31 and the release tab 35 to cover the entire adhesive layer 36 on the second distal end portion 39 and the inner tab portion 34. Alternatively, the mechanical fastener material 31 and the release tab 35 could be spaced from each other if there is substantially no exposed adhesive in the gap formed, for example if there is no adhesive layer 36 on second distal end portion 39 and/or the inner tab portion 34 of the tape tab backing 33.

The first embodiment of the tape tab laminate 40 is shown partially attached to a diaper chassis 1 in FIG. 5. The tape tab backing 33 first distal end portion 37 is attached to the diaper corner 6 by the pressure-sensitive adhesive layer 36. The edge 5 of the diaper corner portion 6 substantially abuts the release tab inner fold 41 as shown, however this is not necessary. It is generally sufficient that the first tab distal end portion 37 has sufficient adhesive surface area in contact with the diaper corner 6 so as to provide a secure engagement. The available surface area of adhesive layer 36 and the first end portion 37 is attached to the diaper when the diaper edge 5 is close to or abutting the release tab inner fold 41.

FIG. 5 depicts an intermediate step in the attachment of the mechanical fastener tape tab laminate 40 to the diaper chassis 1. The completed attachment of the laminate 40 to a diaper is shown in FIG. 6 where the tape tab backing 33 is folded over back onto itself on the opposite side of the corner portion 6 so that the pressure-sensitive adhesive 44 on the outer leg 52 of the release tab attaches to the opposite face of the corner portion 6 securing the mechanical fastener tape tab laminate 40 in the folded condition. The mechanical fastener tape tab laminate 40 remains in this folded condition up to the point in time that the diaper is used. When the diaper is used, the folded over portion of the tape tab laminate 40, comprising the second distal end portion 39 and the inner tab portion 34, is extended from its folded condition at the corner 6 of the diaper by breaking the release tab 35 along the weakened line. The mechanical fastener material 31 is then exposed for use as shown in FIG. 7 without any exposed adhesive 36. Generally, to ensure that the laminate is maintained in its folded over condition prior to use, the line of weakness is located at least 10 mm, preferably at least 15 mm, from where the tape tab laminate is folded 49 back onto itself.

In the embodiment of FIGS. 3–7 the second distal end portion 39 of the tape tab backing 33 is effectively bonded to both faces of the diaper 1 at the diaper corner portion 6 by attachment of the first distal end portion 37 of tape tab backing 33 and by attachment of the outer leg 52 of the release tab 35 to the opposite face of the diaper corner portion 6. The shear forces exerted by attachment of the mechanical fastener material 31 to the loop or opposing mechanical fastener material on the diaper chassis are transferred to both faces of the diaper by the attachment of both the release tab 35 and the backing 33 to the diaper. These forces are transferred from the backing 33 to the release tab 53 via the continuous inner fold 41, which provides what is generally called a "Y-bond". The use of a Y-bond fold 49 and its advantages are described, for example, in U.S. Pat. Nos. 3,848,594 and 4,726,971 and PCT Appln. No. WO/IUS96/12464, the substance of which are substantially incorporated herein by reference. The Y-bond fold 49 provides a very secure, permanent attachment of the mechanical fastener tape tab laminate 40 to the diaper chassis 1 minimizing or eliminating the risk of detachment and providing an even distribution of the attachment forces to both faces of the corner portion 6 of the diaper 1.

A second embodiment of the invention mechanical fastener tape tab laminate 50 is shown in FIGS. 8–12. An expanded view of the second embodiment of mechanical fastener tape tab laminate 50 is shown in FIG. 8. The tape tab backing 53 is provided with a pressure-sensitive adhesive layer 56 that allows for attachment of the mechanical fastener material 31, which mechanical fastener material 31 can optionally contain a further adhesive layer 38, and the release tab 55. The tape tab backing 53 is separated into four portions. The first portion is the first distal end portion 57 which is provided with an exposed portion of the adhesive layer 56 for permanent attachment to the diaper chassis 1. The second portion is an inner tab portion 54 which is attached to the release tab 55. The third portion is the second distal end portion 59 of the tape tab backing 53 which is provided with the releasably fastenable mechanical fastener material 31. The fourth portion is the finger lift portion 52, which also has an exposed portion of the adhesive layer 56.

Generally, the tape tab backing 53 is provided with a continuous pressure-sensitive adhesive layer 56 for ease of manufacturability. However, the inner tab portion 54 and the second distal end portion 59 need not be provided with pressure-sensitive adhesive provided that the mechanical fastener material 31 and/or the release tab 55 are provided with suitable adhesive or other conventional means to attach to the backing 53. The adhesive layer 56 could be intermittently provided on the tape tab backing 53 only in those areas where it is needed. The mechanical fastener material 31 is generally provided with upstanding hook elements suitable for engagement to the mating surface provided on the outside of the diaper, generally, the loop fastener element 4.

The release tab 55 generally comprises a backing 75 provided with a pressure-sensitive adhesive layer 58 an outer face 76. The opposite inner face 77 of the backing can be provided with a suitable release layer or treatment, however such is optional. The release tab 55 is folded into a C-shape provided with an inner fold 60 and an open end 61. The inner fold 60 would generally be adjacent the edge 5 on a diaper when the first distal end portion 57 is attached to the diaper corner portion 6. Generally, the release tab 55 backing 75comprises, a flat film or like web having ends 62, which ends 62 can terminate adjacent the mechanical fastener material 31. Generally only the bottom leg 72 of the C-fold release tab 55 needs to terminate near or adjacent the mechanical fastener material 31 of the inner tab portion 54 when there is an underlying pressure sensitive adhesive layer 56. If pressure sensitive adhesive layer 56 is not provided in the inner tab portion, the location of the release tab 55 ends 62 is not critical as no adhesive needs to be covered, and in certain embodiments release tab 55 could be eliminated or be a flat unfolded film only covering the inner tab portion 54. The tape tab backing 53 in the finger lift portion 52 is folded back onto itself in a Z-shape providing an outer top leg 74, having an exposed portion of adhesive layer 56, and an inner leg 73. The bottom leg of the Z-shape is the unfolded main portion of the tape tab backing 53. The inner leg 73 is created by a first fold 64 of the backing 53. The second outer leg 74 is created by a second fold 65 of the inner leg 73. The outer leg 74 is designed to attach to a surface of the diaper by the exposed portion of adhesive layer 56 as shown in FIG. 11. The outer fold 65 is provided with a weakened zone 66, which allows the Z fold finger lift 52 to be easily broken at this point. Generally, this line of weakness is provided by suitably cutting the tape tab backing intermittently along the line 66 or as otherwise discussed relative to the first embodiment. FIG. 9 shows the assembled laminate shown in the expanded view, where like numerals indicate identical elements.

The second embodiment of the tape tab laminate 50 is shown partially attached to a diaper chassis 1 in FIG. 10. The tape tab backing 53 first distal end portion 57 is attached to the diaper corner 6 by the pressure-sensitive layer 56. The edge 5 of the diaper corner portion 6 substantially abuts the release tab fold 60. However, again it is generally only sufficient that the first distal end portion 57 has sufficient adhesive surface area in contact with the diaper corner 6 so as to provide a secure engagement.

FIG. 10 is an intermediate step in the process of attaching the tape tab laminate 50 to the diaper chassis 1. The completed attachment of the second embodiment tape tab laminate 50 is shown in FIG. 11 where the tape tab backing 53 is folded over back onto itself on the opposite side of the corner portion 6 so that the pressure-sensitive adhesive 67 on the finger lift 52 attaches to the opposite face of the corner portion 6 securing the laminate 50 in the folded condition. The mechanical fastener tape tab laminate is provided in this folded condition up to the point in time that the diaper is used. When the diaper is used, the folded over portion of the tape tab laminate comprising the inner tab portion 54 the second distal end portion 59 and the fingerlift portion, are separated from the corner 6 of the diaper by breaking the finger lift portion 52 along the weakened line 66. The mechanical fastener material 31 is then exposed for use as shown in FIG. 12. The outer leg 74 remains attached to the diaper but with the adhesive not exposed during use of the mechanical fastening tab laminate 50.

Again, in the embodiment of FIGS. 8-12, the second distal end portion 59 of the tape tab backing 53 is effectively bonded to both faces of the diaper 1 at the corner portion 6 in a Y-bond 68, by attachment of both the first distal end tab portion 57 of a tape tab backing and outer leg portion 71 of the release tab 55. The shear forces exerted by attachment of the mechanical fastener element 31 to the loop or opposing mechanical fastener on the diaper chassis are transferred to both faces of the diaper as the release tab 55 is attached to both the backing 53 and the diaper by the inner fold 60 which provides a Y-bond 68. The forces from the tape tab backing 53 are transferred to the diaper from the inner leg 72, attached to the backing 53, to the outer leg 71, attached to the diaper.

Figure 13:
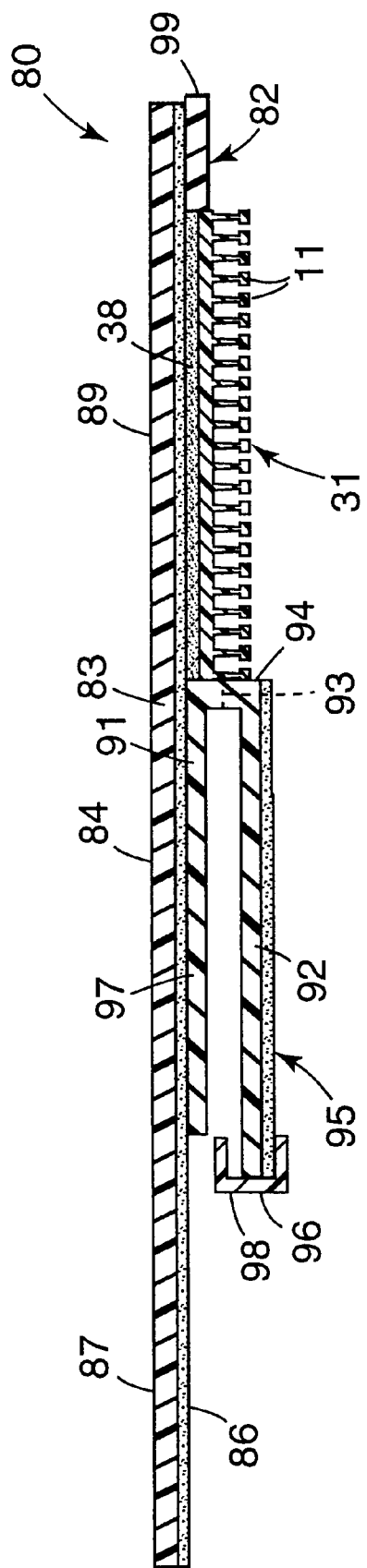
FIG. 13 is a third embodiment of a mechanical fastener tape tab laminate of the invention.

A third embodiment of the invention mechanical fastener tape tab laminate 80 is shown in FIG. 13. The tape tab backing 83 is provided with a pressure sensitive adhesive layer 86 which allows for the attachment of the mechanical fastener material 31, which can optionally contain a further adhesive layer 38, and the release tab laminate 95. The tape tab backing 83 is separated into three portions. The first portion is the first distal tab end portion 87 which is provided with an exposed portion of the adhesive layer 86 for permanent attachment to one face of the diaper chassis 1. The second portion is an inner tab portion 84 which is attached to the release tab 95. The third portion is the second distal end portion 89 of the tape tab backing 83 which is provided with the releasably attachable mechanical fastening material 31. A separately attached web layer 99 attached to the adhesive layer 86 of the tape tab backing 83 provides the optional finger lift 82. The release tab of the embodiment of FIG. 13 differs from the first embodiment of the invention, shown in FIGS. 3–7, in that the release tab backing 97 is folded into a C-fold shape having a first inner leg 91 and a second outer leg 92 on opposite sides of a C-fold 94. The first inner leg 91 of the C-folded release tab is attached to the diaper tape tab backing 83. The second outer leg 92 is not attached to the tape tab backing. The release tab laminate 95 then forms an inner fold 98 by use of a separately attached unifying web 96 forming a tape tab laminate. The unifying web 96 is attached at one face to the second outer leg 92 of the release tab at a terminal end portion of this second outer leg 92, and attached to tape tab backing 83 on an opposite face of the unifying web 96. Between the two points of attachment, the unifying web 96 is folded into a C-shape providing an inner fold 98. This inner fold 98 creates a Y-bond as described in the first embodiment of U.S. Pat. No. 4,726,971, the substance of which is incorporated by reference in its entirety. A. In the FIG. 13 embodiment the release tab 95 laminated with unifying web 96 is a substantially continuous structure from the inner fold 98 provided by the unifying web 96 to the outer C-fold 94 provided by the release tab. The outer C-fold 94 is provided with a weakened zone 93 which allows the release tab to be easily broken at this point after assembled into a diaper as shown in FIG. 1, and the first embodiment FIG. 7.

Figure 14:
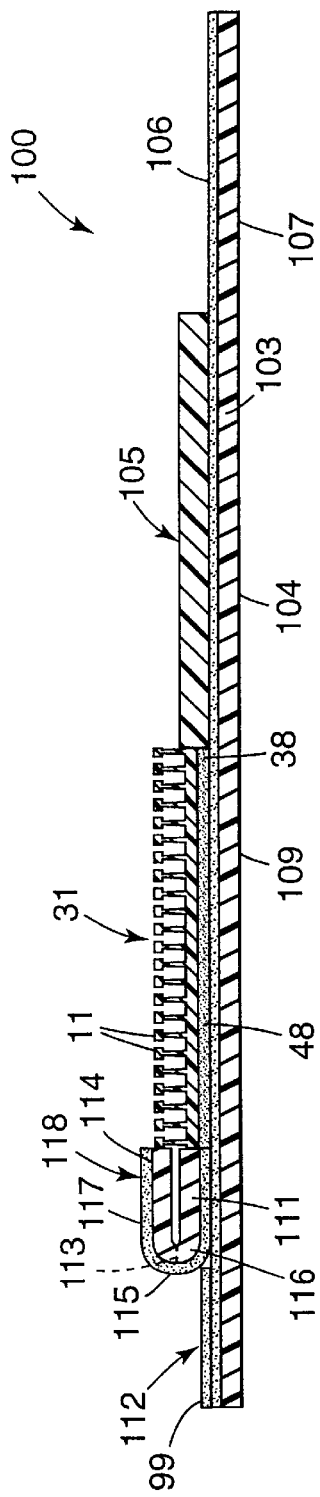
FIG. 14 is an assembled view of fourth embodiment of a mechanical fastener tape tab laminate of the invention.

A fourth embodiment of the invention mechanical fastener tape tab laminate 100 is shown in FIG. 14. The tape tab backing 103 is provided with a pressure sensitive adhesive layer 106 that allows for attachment of the mechanical fastener material 31, which can optionally contain a further adhesive layer 38, and the release tab 105. The tape tab laminate 100 is provided with four portions. The first portion is the first distal end portion 107 which is provided with an exposed adhesive portion of the adhesive layer 106 for a permanent attachment to one face of the diaper chassis 1. The second portion is an inner tab portion 104 which is attached to the release tab 105. The third portion is the second distal end portion 109 of the tape tab backing 103 which is provided with the releasably fastenable mechanical fastener material 31. The fourth portion is a fingerlift portion 112 provided with the breakable line of weakness 113 providing the invention antiflagging feature.

The finger lift portion 112 is provided with a C-folded tape element 118. The C-folded tape element 118 comprises a backing 116 having a first inner leg 111 and a second outer leg 117 separated by fold 115. The second outer leg 117 has an exposed adhesive 114 and the fold 115 is provided with a weakened zone 113, which allows the C-folded tape element 118 to be easily broken at this point. The exposed adhesive layer 114 on the C-folded tape element 118 allows attachment to the opposite face of the diaper corner portion 6 securing the laminate 100 in a folded condition such as shown in the second embodiment of the invention. An adhesive-free fingerlift is provided by web 99 as in the FIG. 13 embodiment. The mechanical fastener tape tab laminate 100 is provided in this folded condition up to the point in time that the diaper is used. When the diaper is used the folded over portion of the tape tab laminate comprising the inner tab portion 104, the second distal end portion 109 and the fingerlift portion 112 are separated from the corner 6 of a diaper by breaking the C-fold tape element 118 along the weakened line 113. The mechanical fastener material 31 is then exposed for use. In this embodiment a Y-bond is not formed in that the release tab 105 is attached only to the tape tab backing 103. The C-folded tape element 118 could also be arranged in the opposite direction such that the open end of the C-fold faces out towards the free fingerlift. Also the first inner leg 111 could be formed by the unfolded tape tab backing 103.

Figure 15:
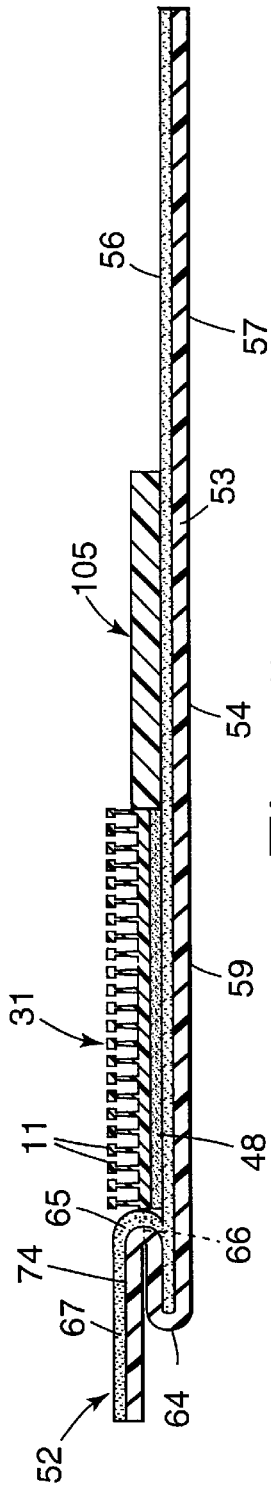
FIG. 15 is an assembled view of fifth embodiment of a mechanical fastener tape tab laminate of the invention.

The embodiment of FIG. 15 is a variation of the second embodiment of the invention where a Y-bond is not created in that a release tab 105 is provided only to cover exposed adhesive on the inner tab portion of the tape tab backing in this embodiment. Like numbers specify identical features of the second embodiment of FIGS. 8–12.

Figure 16:
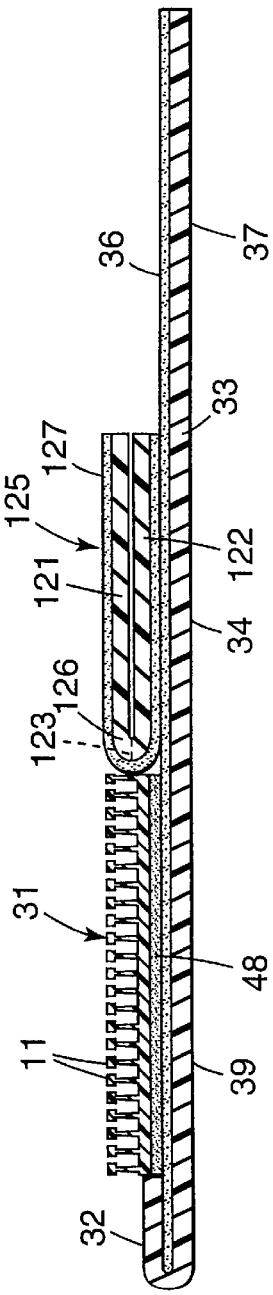
FIG. 16 is an assembled view of sixth embodiment of a mechanical fastener tape tab laminate of the invention.

A sixth embodiment of the invention is shown in FIG. 16. In this embodiment the release tab 125 is provided in a C-fold. An inner leg 122 is attached to the tape tab backing 33 and folded along fold 126 to an outer leg 121, which is provided with an exposed adhesive 127 for attachment to an opposing face of the diaper corner 6. The fold 126 is provided with a line of weakening 123. In this embodiment a Y-bond will not be created in that when the line of weakening 123 is broken the outer leg portion 121 of the release tab would be attached only to the inner face of the diaper and not to the tape tab backing 33.

Figure 17:
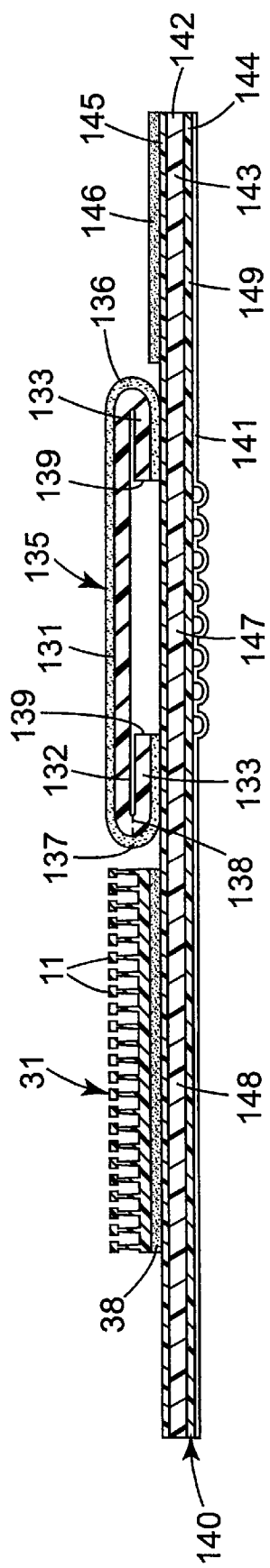
FIG. 17 is an assembled view of the seventh embodiment of a mechanical fastener tape tab laminate of the invention.

A seventh embodiment of the invention is shown in FIG. 17. In this embodiment, the release tab 135 is similar to that shown in the first embodiment except that the tape tab backing 140 is provided with an elastic section 147. Preferably, the two distal end portions of the tape tab backing 140 are inelastic, namely the distal end 148 provided with the mechanical fastener materials 31 and the opposing distal end 149 provided with adhesive layer 146 for permanent attachment of the assembled tab to the diaper chassis 1. The adhesive layer 146 is preferably only provided on the distal end 149 and optionally on distal end 148 but preferably not central elastic portion 147.

The release tab 135 is folded into a circular form with an inner fold 136 and an outer fold 137. The release tab is a substantially continuous structure, as in the first embodiment, when attached to the backing. The outer leg 131 is connected to two inner legs 133, having terminal ends 139, by the two folds 136 and 137. The outer fold 137 is provided with a weakened zone 138 which allows the release tab 135 to be easily broken at this point. The tape tab backing 140 is not covered with an adhesive layer 146, as shown, on the distal end 148 and on the center elastic section 147 so the mechanical fastener material 31 and the release tab 35 can be placed in spaced apart locations without a concern of exposed adhesive.

As in the first embodiment, when the diaper is used, the folded over portion of the tape tab laminate, comprising the second distal end portion 148 and the distal end portion 149, is extended from its folded condition at a corner of the diaper by breaking the release tab 135 along the weakened line 138. The mechanical fastener material 31 is then exposed for use as shown in FIG. 7. Further, the elastic central section 147 is exposed between the two terminal ends 139 of the two inner leg portions 133 of the release tab 135. The two terminal ends 139 are preferably separated by given distance, generally about 1 to 4 cm, preferably 2 to 3 cm, to provide sufficient elastic function to the tape tab laminate. The tab in use as such is elastic by the elastic section 147 of the tape tab backing 140. The tape tab backing can be provided with an elastic section 147 by any known method in the art and is preferably elastic only between the terminal ends of the inner leg portions 133 and not at those portions of the tape tab backing attached to the inner leg portion 133. Relevant methods of providing a tape tab backing with an elastic center section include U.S. Pat. Nos. 3,800,796; 4,074,716; 4,778,701; 4,787,897; 4,795,456; 5,057,097; 5,182,156; 5,344,691; and 5,620,780, the substance of which are incorporated by reference. A further example of a side-by-side coextrusion of a backing having an elastic midsection and inelastic end sections is described in Japanese Kokai 8-187,113 published Jul. 23, 1996. Generally tab backings with elastic sections can be provided by coextrusion of a section that has, or is modified to have, preferential elastic properties or alternatively an elastic material is laminated to one or more inelastic materials. A preferred method of providing an elastic center section in a laminate construction is described in WO99/48455 (corresponding to U.S. application Ser. No. 09/049,727 now U.S. Pat. No. 6,159,584 the substance of which is incorporated by reference) which is the backing material 140 shown in FIG. 17. The tape tab backing 140 comprises a coextruded elastic film formed of an elastic layer 142 and one or more outer inelastic layers, 145 and 144 on the outer face of the elastic layer 142. The coextruded elastic film is laminated to a nonwoven layer 141 which is extensible in at least one section to create the elastic portion 147 of the backing 140 and is relatively inextensible in the areas forming the relatively inelastic distal end portions 148 and 149. The relative extensibly of the nonwoven determines the location of the elastic and inelastic portions of the laminate. The nonwoven 141 can be made to be extensible by mechanical means, such as by forming corrugations, as shown in FIG. 17, or by other known methods. The coextruded elastic film backing 140 and the nonwoven layer 141 can be attached by heat bonding, extrusion bonding, adhesive bonding and the like. Alternatively, the elastic backing 140 could be a single layer elastic film.

The above detailed description of the invention is made with respect to certain preferred embodiments of the invention mechanical fastener tape tab closure laminate as used on a conventional disposable diaper chassis. However, it would be apparent to one of skill in the art that the preferred embodiments of the invention mechanical fastener tape tab closure laminate could be equally applicable to other articles such as hospital gowns, caps, incontinent garments and other diaper designs and the like.

We claim:

1. A mechanical fastener tape tab laminate comprising a tape tab backing having at least a first distal end portion, an inner tab portion and second distal end portion, the second distal end portion provided with a mechanical fastener material, the first distal end portion provided with an adhesive layer for attachment to a disposable absorbent article, the tape tab backing further having a folded tape portion comprising a backing having an adhesive layer on an outer face and having at least an inner leg portion and an outer leg portion, the outer leg portion having an exposed adhesive provided for attachment to the disposable absorbent article, the inner and outer leg portions separated by at least one fold, the folded tape portion backing having a line of weakness along the at least one fold, wherein the line of weakness is provided on a portion of the tape tab backing spaced from the first distal end portion and wherein the folded tape portion has an outer leg portion and two inner leg portions having terminal ends which are separated by a distance and wherein the tape tab backing is elastic for at least a portion of the distance between the terminal ends of the two inner leg portions.

2. The mechanical fastener tape tab laminate of claim 1 wherein the distance between the two terminal ends is from 1 to 4 cm.

3. The mechanical fastener tape tab laminate of claim 2 wherein the distance between the two terminal ends is from 2 to 3 cm.

4. The mechanical fastener tape tab laminate of claim 1 wherein the tape tab backing is elastic only in the region between the terminal ends of the two inner leg portions.

5. The mechanical fastener tape tab laminate of claim 1 wherein the tape tab backing is a laminate of an elastic film and a nonwoven wherein the nonwoven has at least one extensible portion and at least one relatively inextensible portion.

6. A disposable absorbent article having a mechanical fastener tape tab laminate, the disposable absorbent article having an outer face and an inner face at least one edge having a mechanical fastener tape tab laminate at one terminal end, said mechanical fastener tape tab laminate comprising a tape tab backing having at least a first distal end portion, an inner tab portion and second distal end portion, the second distal end portion provided with a mechanical fastener material, the first distal end portion provided with an adhesive layer for attachment to a disposable absorbent article, the tape tab backing further having a folded tape portion comprising a backing having an adhesive layer on an outer face and having at least an inner leg portion and an outer leg portion, the outer leg portion having an exposed adhesive provided for attachment to the disposable absorbent article, the inner and outer leg portions separated by at least one fold, the folded tape portion backing having a line of weakness along the at least one fold, wherein the line of weakness is provided on a portion of the tape tab backing spaced from the first distal end portion and wherein the folded tape portion has an outer leg portion and two inner leg portions having terminal ends which are separated by a distance and wherein the tape tab backing is elastic for at least a portion of the distance between the terminal ends of the two inner leg portions.

7. The disposable absorbent article of claim 6 wherein the distance between the two terminal ends is from 1 to 4 cm.

8. The disposable absorbent article of claim 7 wherein the distance between the two terminal ends is from 2 to 3 cm.

9. The disposable absorbent article of claim 6 wherein the tape tab backing is elastic only in the region between the terminal ends of the two inner leg portions.

10. The disposable absorbent article of claim 6 wherein the tape tab backing is a laminate of an elastic film and a nonwoven wherein the nonwoven has at least one extensible portion and at least one relatively inextensible portion.

* * * * *